United States Patent [19]
Hayes

[11] Patent Number: 5,443,062
[45] Date of Patent: Aug. 22, 1995

[54] LOAD ACTIVATED OXYGEN DELIVERY SYSTEM

[76] Inventor: Jeffrey P. Hayes, 9530 W. Flynn Rd., Indianapolis, Ind. 46231

[21] Appl. No.: 156,368

[22] Filed: Nov. 23, 1993

[51] Int. Cl.⁶ ............................................. A61M 16/00
[52] U.S. Cl. ............................ 128/204.26; 128/205.24
[58] Field of Search ...................... 128/204.23, 204.26, 128/205.24

[56] References Cited

U.S. PATENT DOCUMENTS

| | | | |
|---|---|---|---|
| 4,054,133 | 10/1977 | Myers | 128/205.21 |
| 4,381,002 | 4/1983 | Mon | 128/204.26 |
| 4,575,042 | 3/1986 | Grimland et al. | 251/46 |
| 4,705,034 | 11/1987 | Perkins | 128/204.21 |
| 4,873,971 | 10/1989 | Perkins | 128/204.23 |
| 4,877,023 | 10/1989 | Zalkin | 128/204.26 |
| 4,932,401 | 6/1990 | Perkins | 128/204.26 |
| 5,005,570 | 4/1991 | Perkins | 128/204.23 |
| 5,038,770 | 8/1991 | Perkins | 128/204.23 |
| 5,065,746 | 11/1991 | Steen | 128/204.26 |
| 5,074,298 | 12/1991 | Arnoth | 128/205.24 |
| 5,074,299 | 12/1991 | Dietz | 128/204.23 |
| 5,111,809 | 5/1992 | Gamble et al. | 128/204.26 |
| 5,209,224 | 5/1993 | Nelepka | 128/205.24 |

*Primary Examiner*—Edgar S. Burr
*Assistant Examiner*—Aaron J. Lewis
*Attorney, Agent, or Firm*—Locke Reynolds

[57] ABSTRACT

A load activated oxygen delivery system is configured to deliver oxygen from an oxygen source to a patient through a cannula. The oxygen delivery system includes a precharge chamber for holding oxygen, the precharge chamber having an inlet and an outlet, with the inlet connected to the oxygen source, and a slave chamber providing fluid communication between the cannula and the outlet of the precharge chamber. A diaphragm is positioned to seal the outlet of the precharge chamber to block flow of oxygen from the precharge chamber into the slave chamber. A separate actuating chamber is positioned adjacent to the slave chamber in fluid communication with the diaphragm, with pressure decrease in the actuating chamber relative to the slave chamber causing the diaphragm to move away from the outlet of the precharge chamber, allowing flow of oxygen from the precharge chamber, through the slave chamber, and into the cannula. Decreasing pressure in the actuating chamber is triggered by an electronic pressure sensor that opens a valve.

20 Claims, 3 Drawing Sheets

LOAD ACTIVATED OXYGEN DELIVERY SYSTEM

BACKGROUND AND SUMMARY OF THE INVENTION

The present invention relates to an apparatus for administering oxygen on demand to a patient. More particularly, the present invention relates to an apparatus having a sensor for detecting a patient's inhalation cycle and triggering release of a valve to deliver oxygen to a patient.

Patients having reduced lung function or suffering from pulmonary diseases such as emphysema, bronchitis, and asthma, are commonly treated by delivery of supplemental oxygen. The supplemental oxygen is typically delivered to a patient through a face mask or attached nasal cannula. Currently, for most patients this oxygen is delivered at a determinable constant rate, with oxygen continuously flowing without regard to the breathing cycle of the patient. As will be appreciated, this continuous flow results in substantial waste of oxygen delivered during breath exhalation of the patient. The waste of oxygen is particularly detrimental for patients relying on portable devices that have a limited storage capacity, requiring frequent oxygen recharges that can limit mobility and independence of patients.

To overcome this limitation, devices that deliver oxygen on demand have been proposed. For example, U.S. Pat. No. 4,054,133 to Myers describes a pneumatic control system for regulating the flow of oxygen to a patient. The described system delivers oxygen on demand, and is triggered by the pressure differential between inhalation and exhalation pressure as measured in the nasal cavity. Similarly, U.S. Pat. No. 4,575,,042 to Grimland et al. describes a pneumatically amplified valve that again requires both a sensing tube and an output tube for operation. However, use of such devices is not always convenient, since large, dual lumen cannula are typically required for operation of the device.

As an alternative to the dual lumen, fully pneumatic triggering system, it is possible to use electronic pressure or gas flow sensors to trigger an oxygen administration device. Such electronic sensors advantageously use widely available single lumen cannulas. For example, U.S. Pat. No. 5,005,570 to Perkins describes a device which temporarily stores a premetered, single dose of oxygen, and dispenses the oxygen in synchronization with a patient's inhalation cycle. An electronic sensor is used to produce a signal with the onset of inhalation that delivers electric power to open a valve. This sensor controlled, intermittent opening of the valve allows flow of oxygen through a single cannula to the patient. However, practical application can be limited because of the substantial power requirements for valve operation. Typically, a large solenoid operated valve is required to ensure fast, high volume delivery of oxygen to the patient. These valves require substantial direct current power, and oxygen delivery device manufacturers often must balance short operational battery life against the weight and bulk of additional batteries when designing portable systems.

The present invention overcomes the limitations inherent in dual lumen systems, and the short battery life of the foregoing electronically controlled valve system, by provision of a load activated oxygen delivery system configured to deliver oxygen from an oxygen source to a patient through a single cannula in response to patient inhalation. The oxygen delivery system includes a regulator assembly connectable to the oxygen source, and a main body assembly configured to define a precharge chamber for holding oxygen. The precharge chamber has an inlet and an outlet, with the inlet connected to the regulator assembly. In preferred embodiments, volume of the precharge chamber can be adjusted.

A demand body assembly is attached in fluid communication to the precharge chamber. The demand body assembly is configured to define a slave chamber in fluid communication with the single cannula and an actuating chamber in fluid communication with the regulator. The slave chamber is separated from an actuating chamber by a diaphragm, with the diaphragm positioned to seal the precharge chamber outlet during patient exhalation. The diaphragm moves to an unsealed position during patient inhalation to allow oxygen in the precharge chamber to flow through the precharge chamber outlet into the slave chamber, thereby passing out through the single cannula to the patient.

The present invention does not require an energetically expensive electronic valve or a separate pneumatic line devoted solely to sensing inhalation. Instead, a solenoid assembly or other electronic valve system is positioned in fluid communication with the actuating chamber to open the flow path between the outlet of the precharge chamber and the slave chamber. In effect, the present invention utilizes the power advantage of a pneumatic system without requiring the separate pneumatic triggering line.

The operation cycle of the present invention is initiated by a patient's inhalation. The pressure drop is sensed in the single cannula and the solenoid assembly is energized to open a movable valve. As oxygen pressure in the actuating chamber drops below oxygen pressure in the slave chamber, the pressure differential causes the diaphragm to move away from its sealed position over the precharge chamber outlet. Oxygen quickly flows out from the now unsealed precharge chamber outlet, providing a burst of oxygen in excess of the prescribed continuous flow oxygen rate from the precharge chamber to the patient. This burst of oxygen is necessary to overcome high levels of oxygen that collect in the vicinity of the patient's nasal cavity in "continuous flow" oxygen delivery, which is used to define the patient's prescription flow rate.

In preferred embodiments the flow rate of oxygen can be controlled with the aid of a rotor connected by drive pins to the demand body assembly and positioned in the main body assembly for rotation to a plurality of indexed positions between the regulator assembly and the precharge chamber. The rotor has a calibrated flow path defined therethrough at each indexed position for controlling oxygen flow into the precharge chamber.

In addition to the control of rate and volume of oxygen delivery possible with adjustment to the precharge chamber volume and rotor position, it is also contemplated to employ timing circuits that deactivate the solenoid assembly to close the movable valve prior to completion of patient inhalation. Such a timing circuit prevents wastage of oxygen not deliverable to the lungs before completion of inhalation exhalation by the patient.

Advantageously, the present invention provides an oxygen delivery system that has low power consumption and an extended battery life. Current draw from both the pressure sensor and the valve controlling pressure in the actuating chamber is minimal compared to those devices which directly operate large valves to control oxygen flow.

Another advantage of the present invention is the increased control of oxygen delivery rate, volume, and timing. Adjustments can be made individually and separately to the timing circuit, the volume of the precharge chamber, and the rotor position to provide the best combination that effectively delivers sufficient oxygen to a patient with minimal oxygen wastage.

Additional objects, features, and advantages of the present invention will be apparent upon consideration of the following detailed description and accompanying drawings.

DETAILED DESCRIPTION OF THE INVENTION

Figure 1:
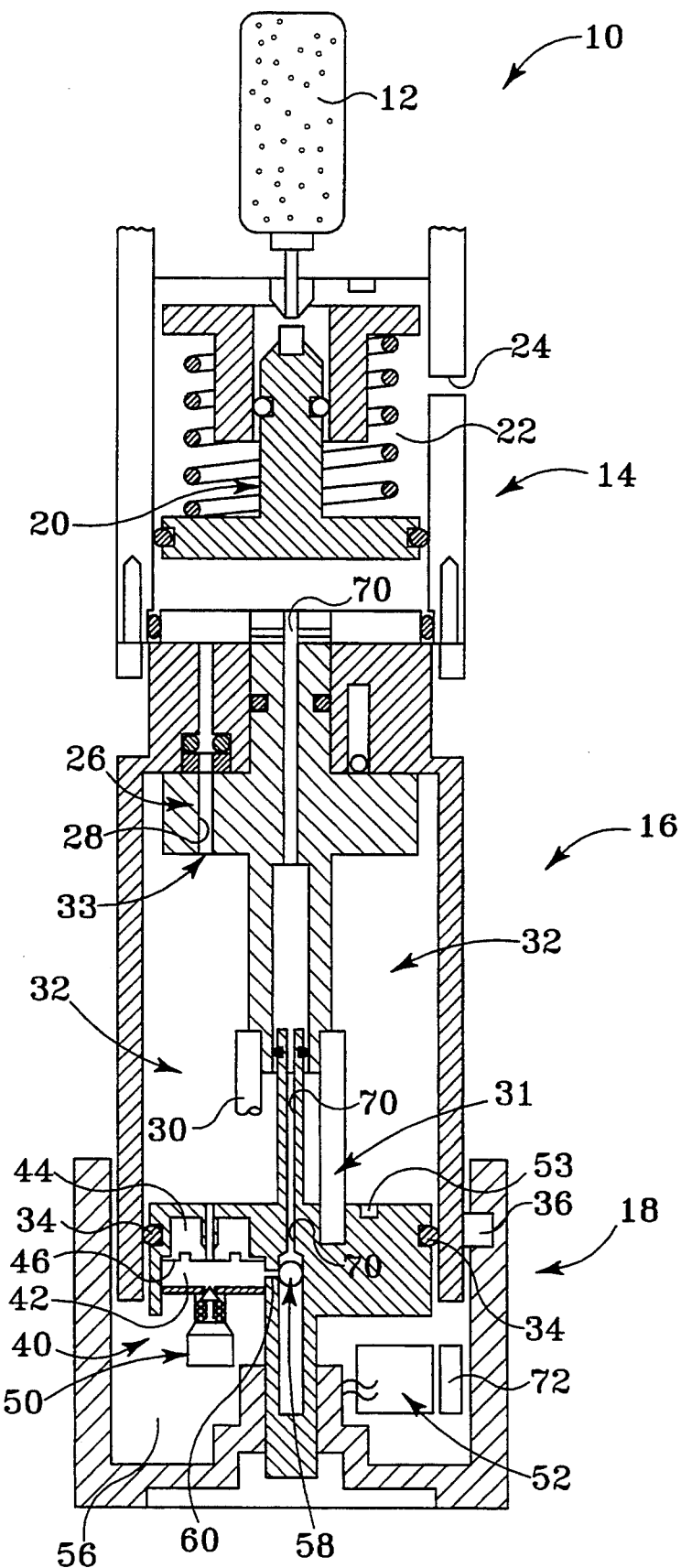
FIG. 1 is a longitudinal cross sectional view along line 1—1 of FIG. 2, showing a load activated oxygen delivery system coupled to a high pressure source of oxygen, with oxygen flow being controlled by a regulator, a metered rotor assembly to provide a calibrated flow path, a precharge chamber to hold a defined volume of pressurized oxygen for fast release into a slave chamber when a sealing diaphragm is moved toward an actuating chamber in response to opening of a demand valve assembly that includes a movable valve controlled by a solenoid assembly, with the solenoid assembly activating in response to a pressure sensor that triggers in response to patient inhalation.

As illustrated in FIGS. 1-4, a load activated oxygen delivery system 10 for connection to an oxygen source 12 includes a regulator assembly 14, a main body assembly 16, and a demand body assembly 18. Together, these assemblies 14, 16, and 18 provide a system for efficiently delivering oxygen to a patient as needed, with minimal loss of oxygen and minimal electric power requirements.

The regulator assembly 14 is of conventional design for engagement with oxygen source 12, and includes a regulator piston 20 and a regulator spring 22. The assembly 14 further defines a regulator relief outlet 24 for overpressure relief. The regulator assembly 14 engages the oxygen source 12, which may include conventional oxygen concentrators, fixed or portable liquid oxygen systems, high pressure oxygen gas cylinders, or hospital or nursing care wall mounted oxygen outlet systems.

The regulator assembly is attached in sealed engagement to the main body assembly 16. The main body assembly 16 is formed to define a precharge chamber 32 that has an inlet 33 and an outlet 48. In addition, a rotor 26 is positioned to extend through the precharge chamber 32. The rotor 26 is driven by drive pins 30 and 31, enabling its selective rotation to a plurality of indexed positions, with each position defining a calibrated flow path 28. Appropriate rotation of the rotor 26 permits varying oxygen flow from the regulator assembly 14 into the precharge chamber 32.

Figure 4:
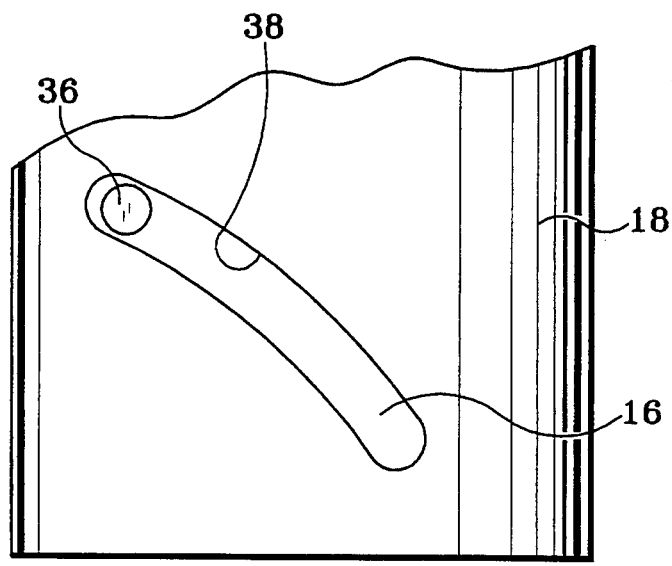
FIG. 4 illustrates pin and channel connection of a main body assembly of the load activated oxygen delivery system to a demand body assembly.

As best seen with reference to FIGS. 1 and 4, the main body assembly 16 is attached in sealing engagement (O-ring seal 34) to the demand body assembly 18. The main body assembly 18 has a permanently attached or integrally formed pin 36 that moves in a curved channel 38 defined through the demand body assembly 18. This pin and channel interaction guides rotation of the demand body assembly 18 relative to the main body assembly 16, and effectively allows adjustment of the volume of the precharge chamber 32. As the demand body assembly 18 is rotated toward the main body assembly 16, the volume of the precharge chamber 32 is reduced. The adjustable precharge chamber is an advantageous feature of the system 10, providing (in conjunction with rotor 26) control over the amount and rate of oxygen delivery from the precharge chamber to a patient.

Figure 2:
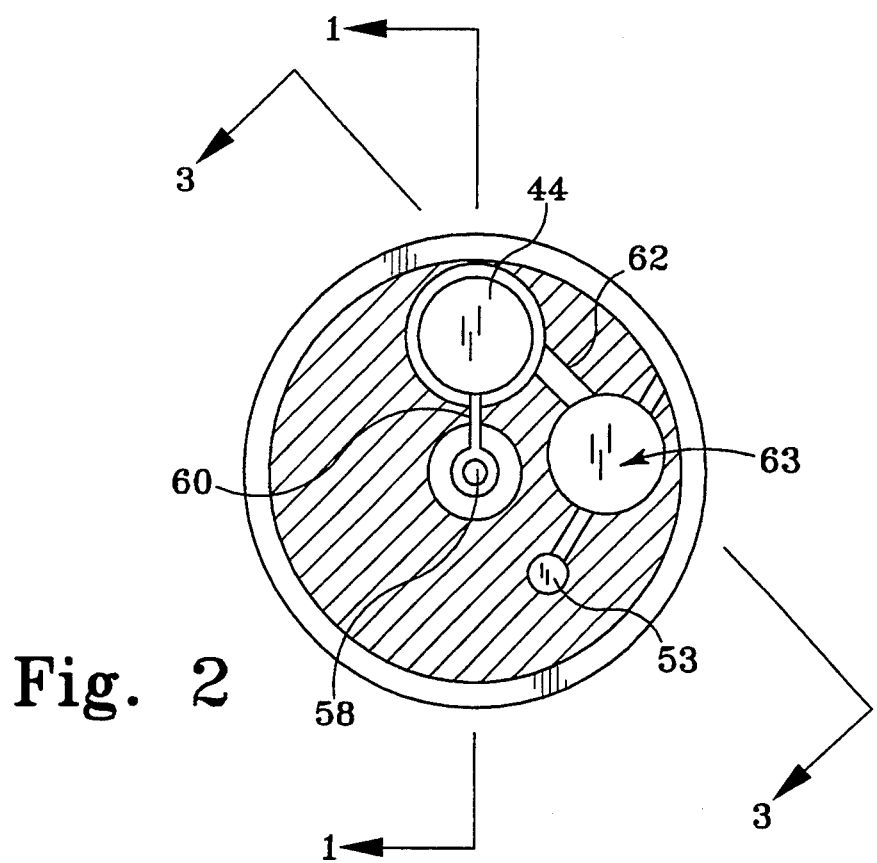
FIG. 2 is a latitudinal cross sectional view of the load activated oxygen delivery system, showing the connection of the slave chamber to a connector chamber, and connection of the actuation chamber to a bleed conduit.
Figure 3:
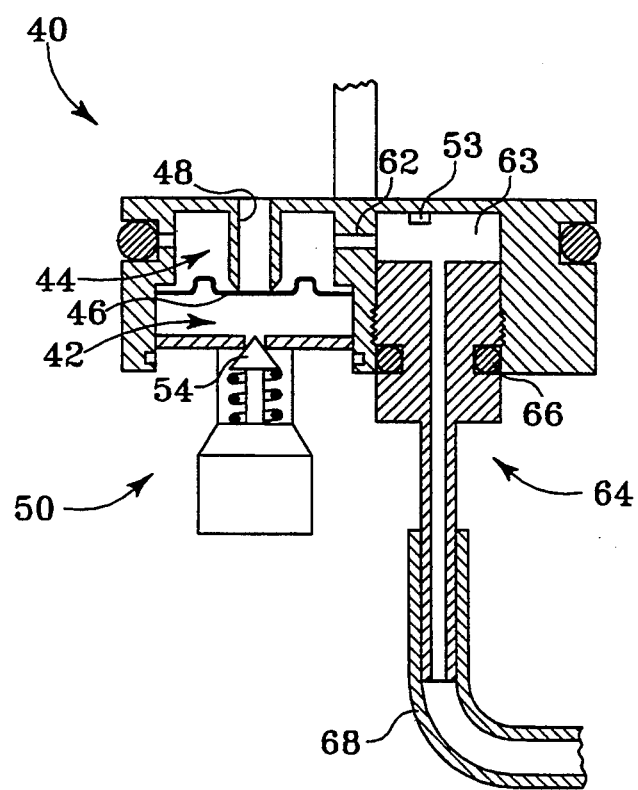
FIG. 3 is an enlarged view of the demand valve assembly shown in FIG. 1, indicating the solenoid assembly, actuating chamber, and slave chamber separated from the actuating chamber by a diaphragm.

As best seen in FIG. 1, and in an enlarged view of FIG. 2, the precharge chamber outlet 48 is positioned in fluid communication with a demand valve assembly 40. The demand valve assembly 40 includes a slave chamber 44 separated from an actuating chamber 42 by a resilient and flexible diaphragm 46. When the actuating chamber 42 is maintained at a greater pressure than the slave chamber 44, the diaphragm 46 seals the precharge chamber outlet 48, preventing oxygen flow into the slave chamber 44. Only when the diaphragm 46 is moved away from the outlet 48 can oxygen in the precharge chamber 32 flow into the slave chamber 44.

Since the slave chamber 44 is in fluid connection with an outflow conduit 62 that leads to a connector chamber 63, any oxygen entering the slave chamber 44 quickly passes out of the slave chamber 44 toward the patient. The connector chamber 63 holds in sealed connection a connector 64 (with O-ring seal 66) that is in turn attached to a single lumen cannula 68. The single lumen cannula 68 receives oxygen flowing from the slave chamber, through the outflow conduit 62 and the connector chamber 63, and into the cannula 68, which is typically positioned to terminate adjacent to a patient's nasal passage to provide intermittent oxygen flow. Alternatively, a face mask or other device positioned adjacent to the patient can be used to deliver oxygen.

As previously noted, before oxygen can flow from the precharge chamber 32 into the slave chamber 44, the diaphragm 46 must be moved away from the precharge chamber outlet 48 by reversing the pressure balance between the slave chamber 44 and the actuating chamber 42. Initially, the pressure in the actuating chamber 42 is higher than the pressure in the slave chamber 44 because of the fluid connection between the oxygen in the regulator assembly 14 and the actuating chamber 42. Fluid communication is maintained by a central passageway 70 that extends from the regulator assembly 14 to the demand valve assembly 40. A short bleed conduit 60 actually connects the central passageway 70 to the actuating chamber 42 as shown in FIG. 2. To more precisely control the rate of pressure increase in the actuating chamber, a calibration ball 58 can be positioned at an appropriate predetermined position adjacent to the bleed conduit 60. Movement of the calibration ball determines the rise in pressure in the actuating chamber 42 when the outlet 48 is sealed by the diaphragm 46.

Reversing the pressure balance between the actuating chamber 42 and the slave chamber 44 is accomplished by use of a low power solenoid assembly 50. The solenoid assembly 50 supports a movable valve 54 that selectively blocks or allows fluid communication between the actuating chamber 42 and a relief chamber 56. Normally biased to present a closed position, when the valve 54 is actively moved to an open position by energization of the solenoid assembly 50, the pressure quickly drops in the actuating chamber 42 as oxygen rushes out to atmosphere through the relief chamber 56. In preferred embodiments, the valve is a low power device employing a small solenoid, although alternative, non-solenoid low power valves may be used such as piezoelectric valves, silicon micro valves, or other conventional low power valves known to those skilled in the art.

The solenoid assembly 50 is triggered to open in response to a signal sent by a pressure sensor 53 supported in the connector chamber 63. The pressure sensor 53 is a conventional low power transducer capable of converting pressure changes, gas flow directionality, or other suitable physical action indicative of patient inhalation, into an electrical signal. The electrical signal activates a conventional timing circuit 52, and powered by a direct current power supply 72 the solenoid assembly 50 is activated for a predetermined time.

In operation, use of the load activated oxygen delivery system 10 simply requires attachment of the regulator assembly 14 to a high pressure source of oxygen 12. Oxygen fills the regulator assembly, and immediately passes through a calibrated flow path 28 in a rotor 26 into a precharge chamber 32, where it remains until the patient inhales. When the patient inhales, a complex train of events occur that result in a burst or pulse of oxygen delivered through the cannula 68 to the patient. First, the sensor 53 detects commencement of inhalation, and sends an electrical signal to a timing circuit. The timing circuit 52 activates, and causes delivery from power supply 72 of sufficient electrical current to activate solenoid assembly 50. The valve 54, pulled by solenoid assembly 50, opens to allow oxygen to rush from the actuating chamber 42 into the relief chamber 56. This reverses the pressure differential between the actuating chamber and the slave chamber, causing the diaphragm 46 separating the two chambers to move away from its seal with the precharge chamber outlet 48. As the seal is broken, oxygen rushes from the precharge chamber 32 into the slave chamber 44, consecutively passing through the outflow conduit 62, the connector chamber 63, the cannula 68, and into the lungs of the patient. After a suitable predetermined period of time, typically before completion of patient inhalation, the timer circuit 52 deactivates the solenoid assembly 50. This causes the valve 54 to again block fluid communication between the actuating chamber and the relief chamber, and causes immediate rise in pressure in the actuating chamber as oxygen passes into the actuating chamber through the bleed conduit 60. The diaphragm 46 moves back to sealing position, and oxygen flow ceases until the beginning of the next inhalation cycle.

While the present invention has been described in connection with specific embodiments, it will be apparent to those skilled in the art that various changes may be made therein without departing from the spirit or scope of the invention.

The claimed invention is:

1. A load activated oxygen delivery system configured to deliver oxygen from an oxygen source to a patient through a cannula in response to patient inhalation, the oxygen delivery system comprising
   a regulator assembly connectable to the oxygen source,
   a main body assembly configured to define a precharge chamber for holding oxygen, the precharge chamber having an inlet and an outlet, with the inlet connected to the regulator assembly,
   a demand body assembly configured to define a slave chamber in fluid communication with the cannula and an actuating chamber in fluid communication with the regulator, the slave chamber being separated from an actuating chamber by a diaphragm, the diaphragm being positioned to seal the precharge chamber outlet during patient exhalation, and the diaphragm moving to an unsealed position during patient inhalation to allow oxygen in the precharge chamber to flow through the precharge chamber outlet into the slave chamber, and
   a demand valve assembly positioned in fluid communication with the actuating chamber, the demand valve assembly including a solenoid assembly which opens a movable valve in response to sensor detection of pressure drop in the cannula as patient inhalation begins, the oxygen pressure in the actuating chamber dropping below oxygen pressure in the slave chamber to permit the diaphragm to move away from its sealed position over the precharge chamber outlet and provide a burst of oxygen from the precharge chamber to the patient.

2. The load activated oxygen delivery system of claim 1, wherein volume of the precharge chamber is adjustable.

3. The load activated oxygen delivery system of claim 2, wherein the volume of the precharge chamber is reduced by moving the demand body assembly toward the main body assembly, and volume of the precharge chamber is increased by moving the demand body assembly away from the main body assembly.

4. The load activated oxygen delivery system of claim 3, further comprising a pin extending from the main body assembly to engage a curved channel defined in the demand body assembly, with interaction of the pin and the curved channel controlling rotation of the demand body assembly toward and away from the main body assembly to adjust volume of the precharge chamber.

5. The load activated oxygen delivery system of claim 1, further comprising a rotor positioned for rotation to a plurality of indexed positions between the regulator assembly and the precharge chamber, the rotor having a calibrated flow path defined therethrough at each indexed position for controlling oxygen flow into the precharge chamber.

6. The load activated oxygen delivery system of claim 5, wherein the rotor is connected by drive pins extending through the main body to the demand body assembly.

7. The load activated oxygen delivery system of claim 1, further comprising means for actuating the solenoid assembly to close the movable valve prior to completion of patient inhalation to prevent wastage of oxygen not deliverable to the lungs before exhalation by the patient.

8. A load activated oxygen delivery system configured to deliver oxygen from an oxygen source to a patient through a cannula, the oxygen delivery system comprising

- a precharge chamber for holding oxygen, the precharge chamber having an inlet and an outlet, with the inlet connected to the oxygen source,
- a slave chamber providing fluid communication between the cannula and the outlet of the precharge chamber,
- a diaphragm positioned to seal the outlet of the precharge chamber to block flow of oxygen from the precharge chamber into the slave chamber,
- an actuating chamber positioned adjacent to the slave chamber in fluid communication with the diaphragm, with pressure decrease in the actuating chamber relative to the slave chamber causing the diaphragm to move away from the outlet of the precharge chamber, allowing flow of oxygen from the precharge chamber, through the slave chamber, and into the cannula, and
- means for reducing pressure in the actuating chamber responsive to signals provided by an electronic pressure sensor in constant fluid communication with the cannula.

9. The load activated oxygen delivery system of claim 8, wherein the pressure reducing means further comprises a demand valve assembly positioned in fluid communication with the actuating chamber, the demand valve assembly including a solenoid assembly that opens a movable valve in response to sensor detection of pressure drop in the cannula as patient inhalation begins, with oxygen pressure in the actuating chamber dropping below oxygen pressure in the slave chamber to permit the diaphragm to move away from its sealed position over the precharge chamber outlet and provide a burst of oxygen from the precharge chamber to the patient.

10. The load activated oxygen delivery system of claim 9, further comprising a regulator assembly connected in fluid communication between the oxygen source and the precharge chamber.

11. The load activated oxygen delivery system of claim 9, wherein the solenoid assembly closes the movable valve prior to completion of patient inhalation to prevent wastage of oxygen not deliverable to the lungs before exhalation by the patient.

12. The load activated oxygen delivery system of claim 10, further comprising a rotor positioned for rotation to a plurality of indexed positions between the regulator assembly and the precharge chamber, the rotor having a calibrated flow path defined therethrough at each indexed position for controlling oxygen flow into the precharge chamber.

13. The load activated oxygen delivery system of claim 8, wherein volume of the precharge chamber is adjustable.

14. A load activated oxygen delivery system configured to deliver oxygen from an oxygen source to a patient through a cannula, the oxygen delivery system comprising

- a precharge chamber for holding oxygen, the precharge chamber having an inlet and an outlet, with the inlet connected to the oxygen source,
- a slave chamber providing fluid communication between the cannula and the outlet of the precharge chamber,
- means for sealing the outlet of the precharge chamber to block flow of oxygen from the precharge chamber into the slave chamber,
- an actuating chamber positioned adjacent to the slave chamber in fluid communication with the sealing means, with pressure decrease in the actuating chamber relative to the slave chamber causing the sealing means to move away from the outlet of the precharge chamber, allowing flow of oxygen from the precharge chamber, through the slave chamber, and into the cannula, and
- means for reducing pressure in the actuating chamber responsive to signals provided by an electronic pressure sensor in constant fluid communication with the cannula.

15. An oxygen delivery system configured to deliver oxygen from an oxygen source to a patient through a cannula, the oxygen delivery system comprising

- a regulator assembly connectable to the oxygen source,
- a main body assembly connected to the regulator assembly, and configured to define a precharge chamber for holding oxygen, the precharge chamber having an inlet connected to the regulator assembly,
- a demand body assembly rotatably coupled to the main body assembly, and configured to define a piston situated within the precharge chamber and including an outlet, and
- means for adjusting the volume of the precharge chamber to control volume of oxygen released from the precharge chamber through the outlet including a pin fixed to the main body assembly and a channel in the demand body assembly receiving the pin and configured to guide the movement of the demand body assembly relative to the main body assembly.

16. The oxygen delivery system of claim 15, wherein the demand body assembly is configured to define a slave chamber in fluid communication with the cannula and an actuating chamber in fluid communication with the regulator, the slave chamber being separated from an actuating chamber by a diaphragm, the diaphragm being positioned to seal the precharge chamber outlet during patient exhalation, and the diaphragm moving to an unsealed position during patient inhalation to allow oxygen in the precharge chamber to flow through the precharge chamber outlet into the slave chamber, and wherein a demand valve assembly is positioned in fluid communication with the actuating chamber, the demand valve assembly including a solenoid assembly which opens a movable valve in response to sensor detection of pressure drop in the cannula as patient inhalation begins, the oxygen pressure in the actuating chamber dropping below oxygen pressure in the slave chamber to permit the diaphragm to move away from its sealed position over the precharge chamber outlet and provide a burst of oxygen from the precharge chamber to the patient.

17. An oxygen delivery system configured to deliver oxygen from an oxygen source to a patient through a cannula, the oxygen delivery system comprising

- a regulator assembly connectable to the oxygen source,
- a main body assembly connected to the regulator assembly,
- a demand body assembly connected to the main body assembly, with the main body assembly and the demand body assembly together defining a precharge chamber for holding oxygen, the precharge chamber having an inlet and an outlet, with the inlet connected to the regulator assembly and the outlet connected to the cannula to deliver a burst of oxygen from the precharge chamber to the patient, the main body assembly and the demand body assembly being rotatably coupled to each other, a pin on one of the body assemblies engaging a channel on the other body assembly configured so that rotation of the demand body assembly relative to the main body assembly adjusts the precharge chamber volume.

18. The oxygen delivery system of claim 17, wherein the volume of the precharge chamber is reduced by moving the demand body assembly toward the main body assembly, and volume of the precharge chamber is increased by moving the demand body assembly away from the main body assembly.

19. The oxygen delivery system of claim 17, further comprising a rotor positioned for rotation to a plurality of indexed positions between the regulator assembly and the precharge chamber, the rotor having a calibrated flow path defined therethrough at each indexed position for controlling oxygen flow into the precharge chamber.

20. The oxygen delivery system of claim 19, wherein the rotor is connected by drive pins extending through the main body to the demand body assembly.

* * * * *